United States Patent
Keenan

(10) Patent No.: US 10,773,028 B2
(45) Date of Patent: Sep. 15, 2020

(54) INDEXING DOSE DISPENSING DEVICE

(71) Applicant: WestRock Dispensing Systems, Inc., Grandview, MO (US)

(72) Inventor: Joseph F. Keenan, Superior, CO (US)

(73) Assignee: Silgan Dispensing Systems Corporation, Grandview, MO (US)

(*) Notice: Subject to any disclaimer, the term of this patent is extended or adjusted under 35 U.S.C. 154(b) by 175 days.

(21) Appl. No.: 15/516,394

(22) PCT Filed: Oct. 7, 2015

(86) PCT No.: PCT/US2015/054456
§ 371 (c)(1),
(2) Date: Apr. 1, 2017

(87) PCT Pub. No.: WO2016/057647
PCT Pub. Date: Apr. 14, 2016

(65) Prior Publication Data
US 2017/0246402 A1 Aug. 31, 2017

Related U.S. Application Data

(60) Provisional application No. 62/060,881, filed on Oct. 7, 2014.

(51) Int. Cl.
| | | |
|---|---|---|
| A61M 5/315 | (2006.01) | |
| A61J 7/00 | (2006.01) | |
| A61M 39/24 | (2006.01) | |
| A61M 5/31 | (2006.01) | |
| A61B 17/00 | (2006.01) | |
| A61B 90/00 | (2016.01) | |

(52) U.S. Cl.
CPC ........ *A61M 5/31593* (2013.01); *A61J 7/0046* (2013.01); *A61M 5/3158* (2013.01); *A61M 5/31515* (2013.01); *A61M 5/31555* (2013.01); *A61M 39/24* (2013.01); *A61B 17/00491* (2013.01); *A61B 2017/00455* (2013.01); *A61B 2090/063* (2016.02); *A61B 2090/0807* (2016.02); *A61B 2090/0811* (2016.02); *A61M 2005/3126* (2013.01); *A61M 2205/581* (2013.01); *A61M 2205/582* (2013.01)

(58) Field of Classification Search
CPC .......... A61M 5/31555; A61M 5/31593; A61M 2005/31518; A61M 5/14566; A61M 2005/14506; A61M 2205/581; A61M 5/3158

See application file for complete search history.

(56) References Cited

U.S. PATENT DOCUMENTS

| | | | | |
|---|---|---|---|---|
| 1,180,858 A | * | 4/1916 | Lefever | F41B 9/004 222/79 |
| 2,180,978 A | * | 11/1939 | Samuel | B05C 17/0123 74/169 |
| 2,229,839 A | * | 1/1941 | Samuel | B05C 17/0123 74/169 |

(Continued)

*Primary Examiner* — Scott J Medway
(74) *Attorney, Agent, or Firm* — Barlow, Josephs & Holmes, Ltd.

(57) ABSTRACT

A dispensing device is disclosed which provides for dispensing multiple doses from a cylindrical volume. An actuator button moves a tooth to engage a series of links which move a stopper to dispense the doses.

18 Claims, 3 Drawing Sheets

(56) References Cited

U.S. PATENT DOCUMENTS

| | | | | |
|---|---|---|---|---|
| 2,233,587 A * | 3/1941 | Samuel | B05C 17/0123 | 74/169 |
| 2,240,046 A * | 4/1941 | Anthony | B05C 17/0113 | 222/391 |
| 2,367,347 A * | 1/1945 | Good | B05C 17/0123 | 74/169 |
| 2,768,768 A * | 10/1956 | Cornell | G01F 11/026 | 222/80 |
| 2,889,085 A * | 6/1959 | Collins | B05C 17/0123 | 222/391 |
| 3,161,325 A * | 12/1964 | Hinkel | A61M 3/00 | 222/80 |
| 3,221,409 A * | 12/1965 | Thiel | A61O 5/62 | 433/83 |
| 3,229,865 A * | 1/1966 | Harold Heisler | B05C 17/0113 | 222/391 |
| 4,126,251 A * | 11/1978 | Subwick | B05C 17/0123 | 222/326 |
| 4,313,439 A * | 2/1982 | Babb | A61M 5/1454 | 128/DIG. 12 |
| 4,318,499 A * | 3/1982 | Hamilton | B05C 17/0113 | 222/327 |
| 4,749,106 A * | 6/1988 | von Schuckmann | B65D 83/0022 | 221/229 |
| 4,805,805 A * | 2/1989 | Ocheskey | B05C 17/005 | 222/102 |
| 4,805,810 A * | 2/1989 | Czetwertynski | B65D 83/0016 | 222/319 |
| 4,917,273 A * | 4/1990 | Seager | A46B 11/0024 | 222/145.3 |
| 4,969,874 A * | 11/1990 | Michel | A61M 5/155 | 604/140 |
| 5,062,551 A * | 11/1991 | Goldstein | A45D 40/02 | 222/390 |
| 5,261,882 A * | 11/1993 | Sealfon | A61M 5/1454 | 128/DIG. 12 |
| 5,335,994 A * | 8/1994 | Weynant Nee Girones | G01K 5/483 | 116/216 |
| 5,501,374 A * | 3/1996 | Laufer | B05C 17/0123 | 222/391 |
| 5,507,727 A * | 4/1996 | Crainich | A61M 5/31595 | 604/97.02 |
| 5,615,807 A * | 4/1997 | Peng | B05C 17/01 | 222/153.01 |
| 5,816,306 A * | 10/1998 | Giacomel | E06B 9/368 | 160/6 |
| 5,919,167 A * | 7/1999 | Mulhauser | A61M 5/14546 | 604/131 |
| 6,110,149 A * | 8/2000 | Klitgaard | A61M 5/24 | 604/207 |
| 6,248,093 B1 * | 6/2001 | Moberg | A61M 5/1456 | 128/DIG. 12 |
| 6,302,869 B1 * | 10/2001 | Klitgaard | A61M 5/31511 | 604/209 |
| 6,321,945 B1 * | 11/2001 | Girouard | B05C 17/0103 | 222/113 |
| 6,457,606 B1 * | 10/2002 | Burke | B05C 17/01 | 222/1 |
| 6,474,219 B2 * | 11/2002 | Klitmose | A61M 5/14566 | 92/137 |
| 6,488,183 B1 | 12/2002 | Braeuninger-Weimer et al. | | |
| 6,824,018 B1 * | 11/2004 | Eaddy | B65D 83/0022 | 222/153.13 |
| 6,945,961 B2 * | 9/2005 | Miller | A61M 5/31525 | 604/207 |
| 7,198,615 B2 * | 4/2007 | Langley | A61M 5/31513 | 604/151 |
| 7,713,238 B2 * | 5/2010 | Mernoe | A61M 5/14244 | 604/131 |
| 7,753,879 B2 * | 7/2010 | Mernoe | A61M 5/14248 | 604/131 |
| 7,785,288 B2 * | 8/2010 | Mernoe | A61M 5/14248 | 604/65 |
| 8,439,930 B2 * | 5/2013 | Campion | A61B 17/8816 | 604/209 |
| 8,540,124 B2 * | 9/2013 | Francavilla | B65D 83/0011 | 222/386 |
| 8,585,657 B2 * | 11/2013 | Colton | A61M 5/1456 | 604/151 |
| 8,876,766 B2 * | 11/2014 | Holmqvist | A61M 5/2033 | 604/135 |
| 9,174,236 B2 * | 11/2015 | Veltrop | B65D 83/0033 | |
| 9,878,345 B2 * | 1/2018 | Hefele | B05C 17/0103 | |
| 10,342,926 B2 * | 7/2019 | Nazzaro | A61M 5/31593 | |
| 10,363,374 B2 * | 7/2019 | Nazzaro | A61M 5/42 | |
| 10,413,667 B2 * | 9/2019 | Henderson | A61M 5/427 | |
| 2002/0004651 A1 * | 1/2002 | Ljunggreen | A61M 5/31501 | 604/218 |
| 2002/0007154 A1 * | 1/2002 | Hansen | A61M 5/20 | 604/207 |
| 2002/0107492 A1 * | 8/2002 | Brach | B65D 35/28 | 604/296 |
| 2003/0212372 A1 * | 11/2003 | Bills | A61C 3/005 | 604/236 |
| 2005/0109799 A1 * | 5/2005 | Catani | B65D 83/0022 | 222/391 |
| 2005/0251097 A1 * | 11/2005 | Mernoe | A61M 5/14244 | 604/221 |
| 2005/0273059 A1 * | 12/2005 | Mernoe | A61M 5/14248 | 604/180 |
| 2007/0073228 A1 * | 3/2007 | Mernoe | A61M 5/14244 | 604/131 |
| 2007/0073236 A1 * | 3/2007 | Mernoe | A61M 5/14244 | 604/151 |
| 2007/0203459 A1 | 8/2007 | Mernoe | | |
| 2007/0185449 A1 | 9/2007 | Mernoe | | |
| 2008/0290115 A1 * | 11/2008 | Amron | F41B 9/0018 | 222/79 |
| 2012/0022499 A1 * | 1/2012 | Anderson | A61M 5/14248 | 604/506 |
| 2015/0290392 A1 * | 10/2015 | Henderson | A61M 5/427 | 604/111 |
| 2017/0340827 A1 * | 11/2017 | Nazzaro | A61M 5/31531 | |
| 2017/0340837 A1 * | 11/2017 | Nazzaro | A61M 5/14248 | |
| 2018/0001032 A1 * | 1/2018 | Kleyman | A61M 5/31578 | |
| 2018/0256823 A1 * | 9/2018 | Nazzaro | A61M 5/14248 | |

* cited by examiner

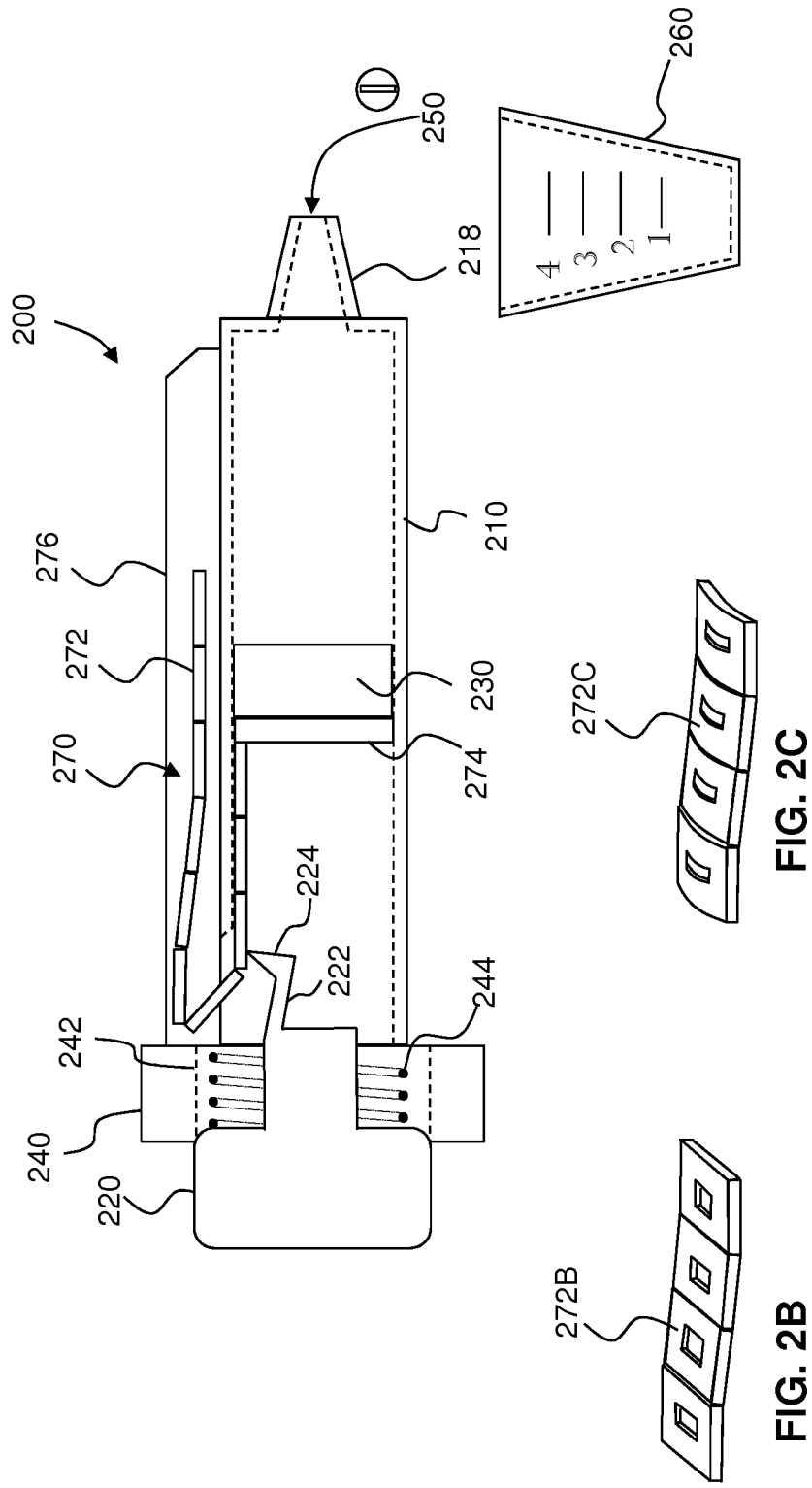

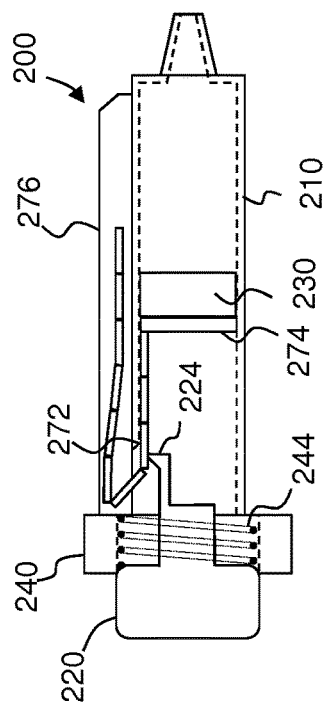
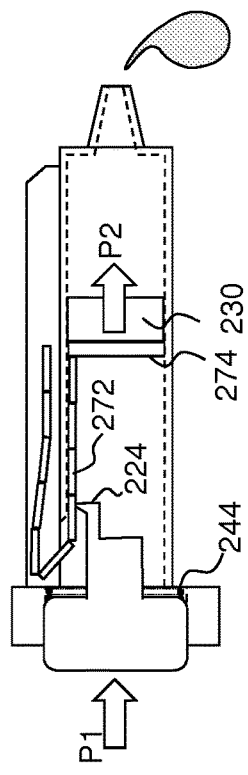
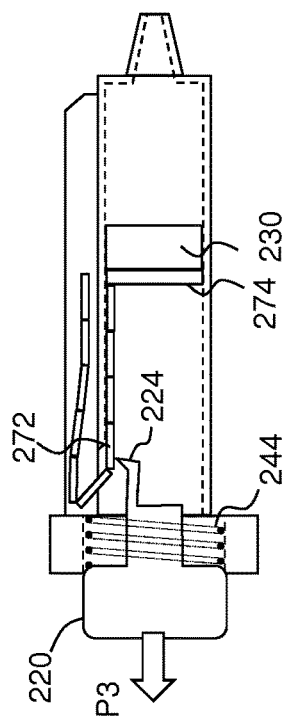
FIG. 3A
FIG. 3B
FIG. 3C

INDEXING DOSE DISPENSING DEVICE

BACKGROUND OF THE INVENTION

The present application is directed to a device for dispensing multiple, sequential amounts of liquids or fluids including semi-solid fluids, such as medication doses, precise aliquots of adhesives, or other useful fluids where a consistent and repeatable dispensing amount is desired.

Products such as fluid medicines, for example cough syrups and the like, may be packaged in containers holding multiple doses that are to be dispensed by pouring the medicine into a spoon or into a small cup. Such methods are prone to spilling and subject to inexact amounts. A more repeatable, neater dispensing method is desired.

It is known to have dispensing devices capable of delivering several measured doses. For example, United States Patent Application Publication 20130289493 to Baney et al discloses a "Dose dividing delivery device," but the device is complex. It would be advantageous to have a delivery device that is simple to manufacture and use.

The dispensing device disclosed here has a simple construction that facilitates its use as a disposable, pre-filled dispensing device.

SUMMARY

In one aspect, a fluid dispensing device is disclosed that include a cylinder, a stopper axially movable through the cylinder, a pusher plate in contact with an outward face of the stopper, a plurality of links connected together in series, with a terminal one of the links connected to the pusher plate, and an actuator tooth movable axially inwardly and outwardly with respect to the cylinder, the actuator tooth on an inward stroke engaging at least one of the plurality of links and causing the stopper to move inwardly through the cylinder, the actuator tooth on an outward stroke disengaging from the plurality of links.

In certain embodiments, each of the plurality of links are of equal length.

In certain embodiments, the length of each link corresponds to a fluid dosage to be delivered by the dispensing device.

In certain embodiments, the links are connected together by living hinges.

In certain embodiments, the fluid dispensing device includes a spring to bias the actuator tooth outwardly with respect to the cylinder.

In certain embodiments, the fluid dispensing device includes an actuator button connected to the actuator tooth.

In certain embodiments, the links are substantially flat.

In certain embodiments, the links are slightly curved in cross section.

In certain embodiments, the fluid dispensing device includes a track housing to contain at least some of the links.

Other aspects of the disclosed fluid dispensing device will become apparent from the following description and the accompanying drawings.

BRIEF DESCRIPTION OF THE DRAWINGS

FIG. 2A shows a side view of the parts of the fluid dispensing device;
FIGS. 2B and 2C show detail views of certain parts of the dispensing device;
and
FIGS. 3A-3C show several views of the fluid dispensing device in use.

DETAILED DESCRIPTION

Figure 1:
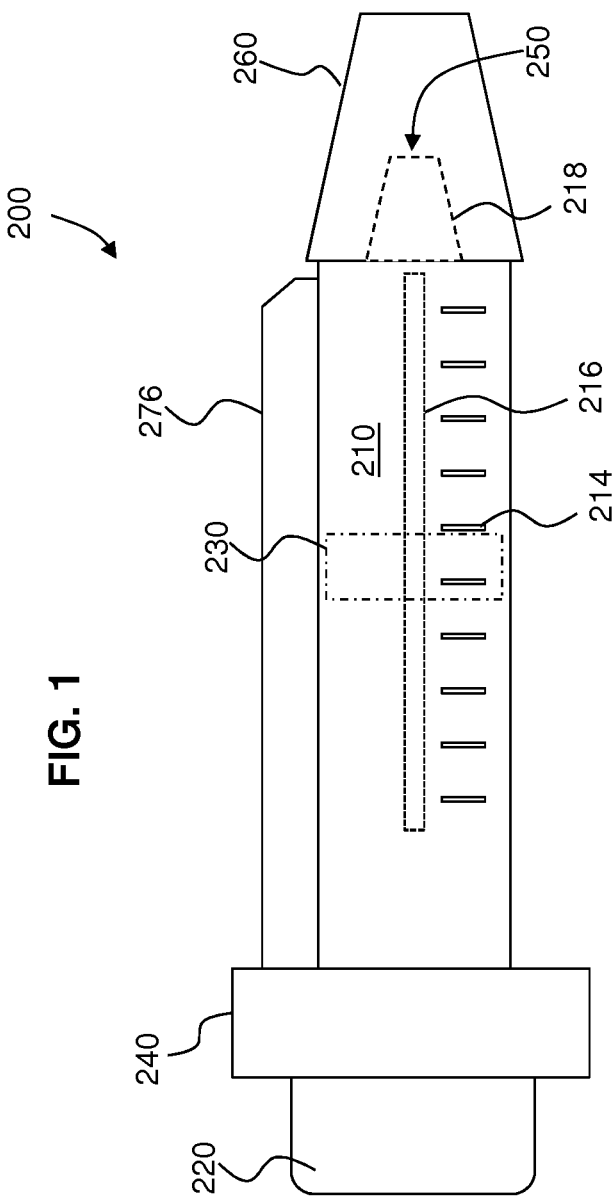
FIG. 1 shows a side view of a fluid dispensing device.

As various embodiments of the fluid dispensing device are described, reference will be made to FIGS. 1-3. Certain parts of the dispensing device are denoted by reference numerals. Where there is more than one of the same feature, generally only one will be denoted by a reference numeral. Where assembly steps are described, these steps are exemplary and are not to be limiting as to the sequence of operations used to arrive at the final package. Also, directions such as up, down, top, bottom, front, back, etc. are used for convenience in describing the device and are not meant to be limiting.

FIG. 1 shows a side view of a dispensing device 200, in an assembled state. The parts include cylinder 210, actuator button 220, stopper 230 (hidden within the cylinder), collar 240, outlet valve 250, cap 260, and actuator track 270 (hidden within track housing 276 in FIG. 1).

Cylinder 210 may by a generally right circular shape, such as a round tube. The cylinder may be made of a material such as a plastic and may be formed by injection molding. The cylinder may have an open end (toward the left in FIG. 1) and distal end (toward the right in FIG. 1). Along at least part of the length of cylinder 210 may be provided gradations 214 such as printed indicia, molded indicia, or transparent, translucent, or opaque areas.

Cylinder 210 may be transparent, translucent, or opaque. If the cylinder is not transparent, at least a portion 216 may be provided which is transparent or translucent in order for a user to see the contents of the cylinder. At the distal end of the cylinder there may be provided an outlet such as nozzle 218. A one way valve or drip-prevention feature such as a slit valve or duckbill valve 250, or split or rolling septum, may be provided within or on the outlet nozzle 218 to seal the product in the cylinder when the delivery device is at rest. Alternately, a spring-loaded valve may be used. An outlet valve, for example a spring-loaded valve, may prevent a child from sucking the contents from the cylinder, and may provide an additional microbial barrier for the contents. A removable cap 260 may be provided to attach onto or fit over the distal end of cylinder 210 and/or nozzle 218. Cap 260 may be used as an auxiliary dispensing device, for example with the dose dispensed into the cap so that it may be poured from the cap into a patient's mouth. The cap may have graduations provided thereon, for example by molding or printing. The cap may be attached to cylinder 210 or nozzle 218 by a child-resistant feature, for example using any of the known child-resistant attachments by which a cap may be attached to a medicine bottle.

As shown in FIG. 2A, stopper 230 may be sized to fit in cylinder 210. Stopper 230 may be made from rubber, plastic, or elastomeric material and may be sized and shaped to provide a close, fluid-tight fit against the inside of cylinder 210. Stopper 230 and/or pusher plate 274 may be long enough to move smoothly through cylinder 210 without tending to turn out of axial alignment with the cylinder.

An actuator track 270 may be provided to push the stopper 230 forward in the cylinder 210. The actuator track 270 may include a series of links 272 connected together with a forward end of the series of links connected to a pusher plate 274 immediately behind stopper 230 (e.g. toward the open or left end of cylinder 210). The length of the series of links may be approximately equal to the useful length of the cylinder 210 through which stopper 230 will move.

The links 272 may be formed of a plastic or polymer material or other somewhat flexible material and may be connected one to another through living hinges, that is, thinned portions capable of flexing. The links 272 may be housed in a track housing 276 which may be provided on the outside of cylinder 210. As shown in FIG. 2B, the links may have a generally flat aspect as with links 272B. As shown in FIG. 2C, the links may have a somewhat curved aspect as with links 272C, in which case actuator track 270 may form a shallow trough-shaped structure which may more readily transfer a pushing force from tooth 224 to pusher plate 274. Some or all of links 272 may have an opening, depression, or protrusion to receive tooth 224 (described below), or the tooth may engage a gap between links such as a gap at a living hinge between links. The living hinges between the 272 links allows actuator track 270 to bend over 180 degrees on itself when pulled around the junction where track housing 276 joins cylinder 210, which allows for a compact construction. However, the living hinges still help provide a relatively rigid actuator track 270 when the links 272 are being pushed between tooth 224 and drive plate 274.

At the open end of the cylinder 210 may be provided an actuator button 220 that may be received in a collar 240. On the inside of collar 240 may be a bore 242 through which actuator button 220 may pass. A spring 244 may be provided to bias the actuator button outward from the collar. A tooth 224 may be provided on a portion of the actuator button extending into the cylinder 210. The tooth 224 may be biased radially outward by a flexing arm 222.

Collar 240 and/or actuator button 220 may be provided with indicia such as symbols or words to indicate how to align the actuator button 220 with collar 240 in order to bring driving tooth 224 into alignment with links 272 so that the dispensing device may be utilized. Thus, a rotary motion of the actuator button 220 may bring the tooth 224 into or out of alignment with links 272. To help rotate button 220, it may be provided with knurling or other texture or raised or depressed areas for better gripping of the button by the user. This ability of the actuator button 220 to be rotated to engage or disengage the driving tooth 224 may be utilized as a child resistant or travel lock option. An audible or tactile indication may be produced when the actuator button has been turned so that the driving tooth 224 is aligned into its engaged position. FIGS. 3A-3C illustrate use of the dispensing device. As shown in FIG. 3A, initially the plunger actuator button may protrude outward (to the left in FIG. 3A) under the force of spring 244. The tooth 224 may engage between two links 272 of the actuator track 270.

As shown in FIG. 3B, inward pressure P1 on actuator button 220 will cause the button to move inward against the force of spring 244, so that tooth 224 forces one of the links 272 further inward into cylinder 210. This in turn forces pusher plate 274 inward, and stopper 230 as well, causing a dose of the fluid contents to be expelled from the nozzle 218. Tooth 224 may engage an opening or a protrusion in a link 272, or may engage a gap between links such as a gap at a living hinge between links. Actuator button 220 may be constructed to provide an audible or tactile indication when the button is depressed to its full stroke. In one manner of operation, the user may push on the actuator button with his thumb while one or more fingers support or grip the collar or the cylinder.

As shown in FIG. 3C, actuator button 220 upon being released will be forced back outward by spring 244. Tooth 224 will disengage from the links of the actuator track, and move back outward until it engages with the next link 272. The dispensing device is then ready for another cycle.

The steps shown in FIGS. 3A-3C may be repeated to eventually deliver several doses, for example, about ten doses for the dispensing device shown in FIGS. 3A-3C.

The dispensing device prevents a user from dispensing more than one dose in one actuation of the button, which may help prevent an overdose of medication. The actuator button stroke length and the pitch of the holes the track links may be designed to give the precise dose, and no more, with each actuation of the device.

Although various aspects of the disclosed dispensing device have been shown and described, modifications may occur to those skilled in the art upon reading the specification.

The invention claimed is:

1. A fluid dispensing device comprising:
    a cylinder;
    a stopper axially movable through said cylinder;
    a pusher plate in contact with an outward face of the stopper;
    a plurality of links connected together in series, with a terminal one of the links connected to the pusher plate and at least one of the plurality of links being disposed outside of the cylinder;
    an actuator tooth disposed within the cylinder and the actuator tooth being movable axially inwardly and outwardly and radially inward and outward, about a pivotable flex arm, with respect to said cylinder, the actuator tooth on an inward stroke engaging an opening in at least one of the plurality of links and causing the stopper to move inwardly through the cylinder, the actuator tooth on an outward stroke disengaging from the plurality of links.

2. The fluid dispensing device of claim 1, wherein each of the plurality of links have a length and each of the plurality of links are of equal length.

3. The fluid dispensing device of claim 2, wherein the length of each link corresponds to a fluid dosage to be delivered by the dispensing device.

4. The fluid dispensing device of claim 1, wherein the plurality of links are connected together by living hinges.

5. The fluid dispensing device of claim 1, further comprising a spring to bias the actuator tooth outwardly with respect to the cylinder.

6. The fluid dispensing device of claim 1, further comprising an actuator button connected to the actuator tooth by the pivotable flex arm.

7. The fluid dispensing device of claim 1, wherein the plurality of links are substantially flat.

8. The fluid dispensing device of claim 1, wherein the plurality of links are curved in cross section.

9. The fluid dispensing device of claim 1, further comprising a track housing to contain at least some of the links.

10. The fluid dispensing device of claim 1, further comprising an outlet valve.

11. The fluid dispensing device of claim 1, wherein the actuator tooth is configured and arranged to directly engage at least one of the plurality of links.

12. The fluid dispensing device of claim 6,
    wherein the cylinder includes a central axis extending through a proximal most end through a distal most end, and
    wherein the actuator button is disposed co-axial with the central axis of the cylinder.

13. The fluid dispensing device of claim 6, further comprising a helical spring configured and arranged to bias the actuator button outward from an actuated configuration to an un-actuated configuration.

14. A fluid dispensing device comprising:
a cylinder;
a stopper axially movable through said cylinder;
a pusher plate in contact with an outward face of the stopper;
a plurality of links connected together in series, with a terminal one of the plurality of links connected to the pusher plate, and wherein each one of the plurality of links are substantially the same size;
an actuator tooth disposed within the cylinder and the actuator tooth being movable axially inwardly and outwardly and radially inward and outward, about a pivotable flex arm, with respect to said cylinder, the actuator tooth on an inward stroke engaging an opening in at least one of the plurality of links and causing the stopper to move inwardly through the cylinder, the actuator tooth on an outward stroke disengaging from the plurality of links; and
a spring to bias the actuator tooth outwardly with respect to the cylinder.

15. The fluid dispensing device of claim 14, wherein the plurality of links are connected together by living hinges.

16. A fluid dispensing device comprising:
a cylinder;
a track housing disposed outside of the cylinder;
a stopper axially movable through said cylinder;
a pusher plate in contact with an outward face of the stopper;
a plurality of links connected together in series, with a terminal one of the plurality of links connected to the pusher plate, and at least one of the plurality of links being disposed within the track housing;
an actuator tooth disposed within the cylinder and the actuator tooth being movable axially inwardly and outwardly and radially inward and outward, about a pivotable flex arm, with respect to said cylinder, the actuator tooth on an inward stroke engaging an opening in at least one of the plurality of links and causing the stopper to move inwardly through the cylinder, the actuator tooth on an outward stroke disengaging from the plurality of links.

17. The fluid dispensing device of claim 16, wherein the plurality of links are connected together by living hinges.

18. The fluid dispensing device of claim 16, further comprising a spring to bias the actuator tooth outwardly with respect to the cylinder.

* * * * *